(12) United States Patent
Gerlach et al.

(10) Patent No.: US 12,392,723 B2
(45) Date of Patent: Aug. 19, 2025

(54) METHOD AND DEVICE FOR DETECTING A PRESENCE OF A FLUORESCENCE PATTERN TYPE ON AN ORGAN SEGMENT VIA IMMUNOFLUORESCENCE MICROSCOPY

(71) Applicant: EUROIMMUN Medizinische Labordiagnostika AG, Lübeck (DE)

(72) Inventors: Stefan Gerlach, Lübeck (DE); Jens Krauth, Lübeck (DE); Christian Marzahl, Lübeck (DE); Christopher Krause, Lübeck (DE); Jens Hocke, Lübeck (DE); Maick Danckwardt, Lübeck (DE); Melanie Hahn, Lübeck (DE); Jörn Voigt, Lübeck (DE)

(73) Assignee: EUROIMMUN Medizinische Labordiagnostika AG, Lübeck (DE)

( * ) Notice: Subject to any disclaimer, the term of this patent is extended or adjusted under 35 U.S.C. 154(b) by 305 days.

(21) Appl. No.: 17/895,311

(22) Filed: Aug. 25, 2022

(65) Prior Publication Data

US 2023/0071078 A1 Mar. 9, 2023

(30) Foreign Application Priority Data

Sep. 7, 2021 (EP) .................................. 21195352

(51) Int. Cl.
*G01N 21/64* (2006.01)
*G01N 33/58* (2006.01)
(Continued)

(52) U.S. Cl.
CPC ..... *G01N 21/6458* (2013.01); *G01N 21/6486* (2013.01); *G01N 33/582* (2013.01);
(Continued)

(58) Field of Classification Search
CPC .......... G01N 21/6458; G01N 21/6486; G01N 33/582; G01N 33/564; G06N 3/045;
(Continued)

(56) References Cited

U.S. PATENT DOCUMENTS

| 8,637,327 B2 | 1/2014 | Winfried et al. |
| 11,367,187 B2 | 6/2022 | Krauth et al. |

(Continued)

FOREIGN PATENT DOCUMENTS

| EP | 3258247 A1 | 12/2017 |
| EP | 3712618 A1 | 9/2020 |
| EP | 3767587 A1 | 1/2021 |

*Primary Examiner* — Huy C Ho
(74) *Attorney, Agent, or Firm* — Bochner PLLC; Andrew Bochner

(57) ABSTRACT

There is proposed a method for detecting a presence of a fluorescence pattern type on an organ segment via immunofluorescence microscopy and digital image processing. The steps comprise: provision of the organ segment, incubation of the organ segment with a liquid patient sample, incubation of the organ segment with secondary antibodies which have been labelled with a fluorescent dye, acquisition of a fluorescence image of the organ segment in a colour channel corresponding to the fluorescent dye, and provision of the fluorescence image to a neural network. What takes place by means of the neural network is simultaneous determination of segmentation information through segmentation of the fluorescence image and, furthermore, of a measure of confidence indicating an actual presence of the fluorescence pattern type. What further takes place is determination, on the basis of the previously determined segmentation information, of at least one sub-area of the fluorescence image that is relevant to formation of the fluorescence pattern type, determination, on the basis of the previously determined at least one sub-area, of validity information indicating a degree of a validity of the measure of confi- (Continued)

dence, and output of the measure of confidence depending on the validity information.

9 Claims, 11 Drawing Sheets

(51) Int. Cl.
    *G06N 3/045*     (2023.01)
    *G06T 7/00*     (2017.01)
    *G06T 7/11*     (2017.01)
    *G06T 7/62*     (2017.01)

(52) U.S. Cl.
    CPC ........... *G06N 3/045* (2023.01); *G06T 7/0012* (2013.01); *G06T 7/11* (2017.01); *G06T 7/62* (2017.01); *G06T 2207/10056* (2013.01); *G06T 2207/10064* (2013.01); *G06T 2207/20084* (2013.01); *G06T 2207/30024* (2013.01)

(58) Field of Classification Search
    CPC ......... G06N 3/084; G06T 7/0012; G06T 7/11; G06T 7/62; G06T 2207/10056; G06T 2207/10064; G06T 2207/20084; G06T 2207/30024; G06T 2207/10024; G06T 2207/20081; G06F 18/2414; G06V 10/44; G06V 20/695; G06V 20/698
    USPC ......................................................... 382/128
    See application file for complete search history.

(56) References Cited

U.S. PATENT DOCUMENTS

| | | | |
|---|---|---|---|
| 2010/0047811 A1* | 2/2010 | Winfried | G06T 7/90 435/7.1 |
| 2020/0300764 A1 | 9/2020 | Gerlach et al. | |
| 2021/0169315 A1* | 6/2021 | Mizoguchi | G01N 21/6486 |
| 2022/0082567 A1 | 3/2022 | Gerlach et al. | |

* cited by examiner b)

| N=78 | pos | neg | | |
|---|---|---|---|---|
| Epa-Classifier ASMA pos | 19 | 2 | Sensitivity | 0,90 |
| Epa-Classifier ASMA neg | 2 | 55 | Specificity | 0,96 |

TAB

METHOD AND DEVICE FOR DETECTING A PRESENCE OF A FLUORESCENCE PATTERN TYPE ON AN ORGAN SEGMENT VIA IMMUNOFLUORESCENCE MICROSCOPY

The invention relates to a method and device for detecting a potential presence of a fluorescence pattern type on an organ segment via immunofluorescence microscopy and via digital image processing.

Immunofluorescence microscopy or indirect immunofluorescence microscopy is an in vitro test for determination of a presence of human antibodies against particular antigens in order to be able to answer or assess a diagnostic question. Such antigens are, for example, present in particular regions of organ segments such as those of a rat stomach. The substrate used is thus an organ segment which is incubated with a patient sample in the form of blood or dilute blood or else blood serum or dilute blood serum. The patient sample thus potentially comprises particular primary antibodies which can express a presence of a disease of the patient. Such primary antibodies or specific antibodies can then bind to antigens of the substrate or organ segment. Primary antibodies bound in such a manner can then be labelled in that so-called secondary antibodies, preferably anti-human antibodies, bind to the bound primary antibodies in a further incubation step and can be visualized later as a result of the secondary antibodies having been labelled with a fluorescent dye. Such a fluorescent dye is preferably a green fluorescent dye, especially the fluorescent dye FITC. Such binding of a primary antibody together with a fluorescently labelled secondary antibody can then be visualized later by irradiating the organ segment with excitation light of a particular wavelength and thus exciting the bound fluorescent dyes to emit fluorescence radiation.

Depending on the diagnostic question, the focus can be on a presence of a fluorescence pattern type or specific fluorescence pattern types on particular organ segments or specific sub-regions or sub-areas of the organ segments. The task that thus arises is that of detecting, via digital image processing in the course of immunofluorescence microscopy for an organ segment incubated as specified, one or more fluorescence pattern types in an immunofluorescence microscopy fluorescence image.

FIG. 8 shows a fluorescence image of a stomach of a rat as an example of an organ segment. Such an organ segment comprises different organ layers. Organ layers here are, for example, the so-called mucous layer SC2 or mucosa containing parietal cells and interglandular contractile fibrils, also known as the tunica mucosa.

A further organ layer is, for example, the annular and longitudinal muscle, also known as the tunica muscularis SC1. A further organ layer is, for example, the so-called movement layer, also known as the submucosa SC3. Yet another organ layer is, for example, the muscularis mucosae SC4. Yet another organ layer is, for example, the vessels SC5.

In the case of an anti-smooth muscle antibody pattern (ASMA) as an example, two particular organ layers are relevant to detection of the pattern: firstly, tunica muscularis and, secondly, tunica mucosa. It is via detection of a presence of the ASMA pattern that a physician or expert can then possibly subsequently infer the presence of a hepatitis disease.

A presence of a so-called ASMA pattern becomes apparent in that the two aforementioned organ layers exhibit respective particular sub-fluorescence patterns which together form the fluorescence pattern ASMA. In particular, the focus here is on a combination of a net-like or grid-like pattern in the organ layer tunica muscularis and also a pattern of fine lines (interglandular contractile fibrils) on the organ layer tunica mucosa. It is therefore necessary for these two aforementioned organ layers to be present in the fluorescence image to a sufficient degree or with a sufficient sub-area based on the total area of the fluorescence image, so that a presence of the ASMA pattern can be reliably detected via digital image processing.

The inventors have thus recognized that the principle of immunofluorescence microscopy based on organ segments involves the occurrence of certain negative effects during production that can interfere with reliable detection of a presence of a fluorescence pattern by image processing. An organ segment like the one from FIG. 8 may not comprise the two aforementioned organ layers at a sufficient area fraction in each case. Owing to production errors, what can occur is that at least one of the two layers or else both layers are respectively present only at a very low area fraction in the fluorescence image. Detection of the fluorescence pattern via digital image processing and neural networks may then possibly lead to erroneous results, which should be avoided.

In the production process, there is limited availability of necessary organ material. A relatively large organ segment is first applied to a support surface and the support surface is then divided into partial support surfaces on glass, preferably by cutting, and so it is precisely in certain regions of the organ segment that there may be only partial coverage of the slide. Therefore, in the course of production, it may be possible for particular organ layers to be present in the organ segment only at a low proportion.

Alternatively or additionally, a further negative technical effect can occur: for sufficient depiction or detectability of patterns in a fluorescence image, the fluorescence images are sometimes acquired using microscope optical systems of a particular optical magnification. This can lead to a fluorescence image which captures or depicts neither the entire slide nor the entire organ segment. This, too, can result in a particular organ layer being present in the fluorescence image of the organ segment only at a low proportion.

There is therefore proposed a method according to the invention for detecting a potential presence of a fluorescence pattern type on an organ segment via immunofluorescence microscopy and via digital image processing.

The method comprises various steps. What first takes place is provision of the organ segment on a slide. What then takes place is incubation of the organ segment with a liquid patient sample which potentially comprises primary antibodies. What further takes place is incubation of the organ segment with secondary antibodies which have been labelled with a fluorescent dye. What then takes place is acquisition of a fluorescence image of the organ segment in a colour channel corresponding to the fluorescent dye. What further takes place is provision of the fluorescence image to a neural network.

The method is distinguished by simultaneous determination, by means of a neural network, of segmentation information through segmentation of the fluorescence image and, furthermore, of a measure of confidence indicating an actual presence of the fluorescence pattern type.

What further takes place is determination, on the basis of the previously determined segmentation information, of at least one sub-area of the fluorescence image that is relevant to formation of the fluorescence pattern type.

What further takes place is determination, on the basis of the previously determined at least one sub-area, of validity information indicating a degree of a validity of the measure of confidence.

What further takes place, lastly, is output of the measure of confidence of the actual presence of the fluorescence pattern type depending on the validity information.

There now follows a more detailed description of various aspects of the method according to the invention to illustrate one or more possible advantages.

As already explained above, different problems can occur when preparing organ segments on slides, with the result that organ layers relevant to a pattern or fluorescence pattern to be detected are not present with a sufficient degree of coverage or sufficient sub-areas. Since the method according to the invention checks whether a particular organ layer is present to a sufficient degree as a sub-area relevant to formation of the fluorescence pattern type and since the validity information is then determined on the basis of the previously determined sub-area, it is possible to appropriately control or influence the output of the measure of confidence. In other words: the measure of confidence can be checked on the basis of the sub-area. A particular sub-area thus corresponds to a particular organ layer. The sub-area of the fluorescence image is thus especially a sub-area which is assigned to a particular organ portion or a particular organ layer on the basis of the segmentation information. In other words: the sub-area is determined as a sub-area which represents a particular organ layer, said sub-area or said organ layer being determined on the basis of the segmentation information.

Thus, by checking the sub-area, it can therefore be ensured that the determined measure of confidence with regard to the presence of the fluorescence pattern type is also valid, since, in the event of for example the sub-area or the organ layer having an excessively small size or being excessively small in dimension, the measure of confidence can be detected as invalid.

For example, in the event of the sub-area being too small, it is preferably possible for the measure of confidence not to be output.

Furthermore, the proposed method is especially advantageous for a further reason. The one neural network simultaneously determines the segmentation information based on the fluorescence image and also the measure of confidence for the presence of the fluorescence pattern type. Thus, the neural network is conceived such that not only information about the fluorescence pattern but also at least one particular visible organ layer or sub-area thereof can be simultaneously incorporated in the analysis by the neural network in determining the measure of confidence with regard to the presence of the fluorescence pattern type. In other words: the neural network is a pretrained neural network which, during training, has learnt not only measures of confidence with respect to a presence of the fluorescence pattern type, but also segmentation information based on segmentation of the fluorescence image. Here, the segmentation information represents especially a plurality of sub-segmentation information which each separately represent respective different organ layers of the organ segment.

According to this very invention, it is precisely image processing as known from the prior art that is not carried out: here, in the prior art, so-called masks in the form of image segments or as segmentation information can first be determined and can then be placed over the actual fluorescence image before a neural network then analyses only those masked sub-regions of the fluorescence image that were filtered out by the mask or the segmentation information in order to determine a measure of confidence. Here, the segmentation information would thus first be determined definitively and then subsequently be applied as a mask to the fluorescence image, and be taken into account in the analysis or the determination of the measures of confidence with respect to the presence of the fluorescence pattern only by means of masking of determined sub-image regions of the fluorescence image.

Such a method according to the prior art is not pursued by this very invention, since the segmentation information and the measure of confidence are determined by the neural network in precisely a simultaneous manner. In particular, what is preferably first carried out in the method according to the invention is transformation of the fluorescence image into the so-called feature space by transformation of the fluorescence image by means of at least one convolutional operation, and it is only after said transformation into the feature space that the resultant feature information is then further processed in order to determine, on the basis of said feature information, both the segmentation information and the measure of confidence. In this preferably designed method according to a preferred embodiment, there is then thus precisely no placement of the segmentation information or segmentation masks over the fluorescence image; instead, the determination of the segmentation information and the determination of the measure of confidence are mutually dependent in the processing in the neural network. As a result, it is precisely in a training phase of the neural network that the determination of the measure of confidence can preferably be advantageously influenced in that the likewise simultaneously determined segmentation information influences the determination of the measure of confidence and therefore implicitly particular segmentation information or particular organ layers can be emphasized or taken into greater account. A further advantage is, in particular, that the training of the neural network does not take place in two separate steps; instead, what is simultaneously brought about by the training is optimization of the neural network with respect to segmentation and to determination of the measure of confidence.

Advantageous embodiments of the invention are subject matter of the dependent claims and are more particularly elucidated in the following description with some reference to the figures.

Preferably, the method comprises further steps of: determining, on the basis of the segmentation information, multiple sub-areas of the fluorescence image that are relevant to formation of the fluorescence pattern type, and determining, on the basis of the previously determined sub-areas, validity information indicating a degree of a validity of the measure of confidence.

Preferably, the method comprises further steps of: determining an area fraction of the at least one sub-area based on the area of the fluorescence image, and determining the validity information on the basis of the area fraction.

Preferably, the method comprises further steps of: determining respective area fractions of the respective sub-areas based on the area of the fluorescence image, and determining the validity information on the basis of the area fractions.

Preferably, the method comprises further steps of: determining, on the basis of the segmentation information, multiple sub-areas of the fluorescence image that are relevant to formation of the fluorescence pattern type, determining respective area fractions of the respective sub-areas based on the area of the fluorescence image, determining the validity information on the basis of the area fractions and on the basis of respective threshold values, outputting the measure of confidence of the actual presence of the fluorescence pattern type if the respective area fractions exceed a respective threshold value.

Preferably, the neural network is designed in such a way that it first generates, on the basis of the fluorescence image, a first set of a plurality of feature information in a feature space by means of at least one or more convolutional operations and then determines, on the basis of the first set of feature information, the segmentation information and the measure of confidence.

Preferably, the neural network is designed in such a way that it first generates, on the basis of the fluorescence image, a first set of a plurality of feature information in a feature space by means of one or more convolutional operations, then determines, on the basis of the first set of feature information, the segmentation information, and then determines, on the basis of the first set of feature information and on the basis of the segmentation information, the measure of confidence.

Preferably, the neural network is designed in such a way that it first generates, on the basis of the fluorescence image, a first set of a plurality of feature information in a feature space by means of one or more convolutional operations, then determines, on the basis of the first set of feature information, the segmentation information, then generates, on the basis of the segmentation information, a second set of a plurality of feature information in a feature space by means of at least one convolutional operation, and then determines, on the basis of the first set of feature information and the second set of feature information, the measure of confidence.

Preferably, the method comprises further steps of: determining, on the basis of the segmentation information, multiple sub-areas of the fluorescence image that are relevant to formation of the fluorescence pattern type, and, in the event of the fluorescence pattern type being determined as actually present, determining a degree of brightness of one of the sub-areas in the fluorescence image that is potentially relevant to formation of the fluorescence pattern type, and estimating a maximum degree of dilution of the patient sample at which incubation of the organ segment with the patient sample still leads to a presence of a fluorescence pattern type or the fluorescence pattern type.

There is further proposed a device for detecting at least one potential presence of at least one fluorescence pattern type on an organ segment via immunofluorescence microscopy and via digital image processing, comprising a holding device for a slide containing an organ segment which has been incubated with a patient sample potentially comprising primary antibodies and furthermore with secondary antibodies which have each been labelled with a fluorescent dye, at least one image acquisition unit for acquiring a fluorescence image of the organ segment in a colour channel corresponding to the fluorescent dye. The device further comprises at least one computing unit designed to provide the fluorescence image to a neural network, to simultaneously determine, by means of the one neural network, segmentation information through segmentation of the fluorescence image and, furthermore, a measure of confidence indicating an actual presence of the fluorescence pattern type, to determine, on the basis of the segmentation information, at least one sub-area of the fluorescence image that is relevant to formation of the fluorescence pattern type, to determine, on the basis of the previously determined at least one sub-area, validity information indicating a degree of a validity of the measure of confidence (KM), and to output the measure of confidence of the actual presence of the fluorescence pattern type depending on the validity information.

There is further proposed a method for digital image processing, comprising the steps of: receiving a fluorescence image representing staining of an organ segment due to a fluorescent dye, providing the fluorescence image to a neural network, simultaneously determining, by means of the one common neural network, segmentation information through segmentation of the fluorescence image and a measure of confidence indicating an actual presence of the fluorescence pattern type, determining, on the basis of the segmentation information, at least one sub-area of the fluorescence image that is relevant to formation of the fluorescence pattern type, determining, on the basis of the previously determined at least one sub-area, validity information indicating a degree of a validity of the measure of confidence, outputting the measure of confidence of the actual presence of the fluorescence pattern type depending on the validity information.

There is further proposed a computer program product comprising commands which, upon execution of the program by a computer, prompt said computer to carry out the method for digital image processing.

In what follows, the invention will be more particularly elucidated on the basis of specific embodiments without restricting the general concept of the invention, with reference to the figures. In the figures.

Figure 3:
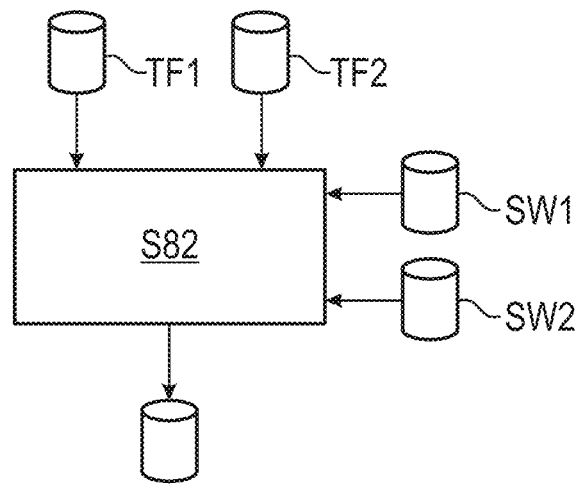
Figure 4:
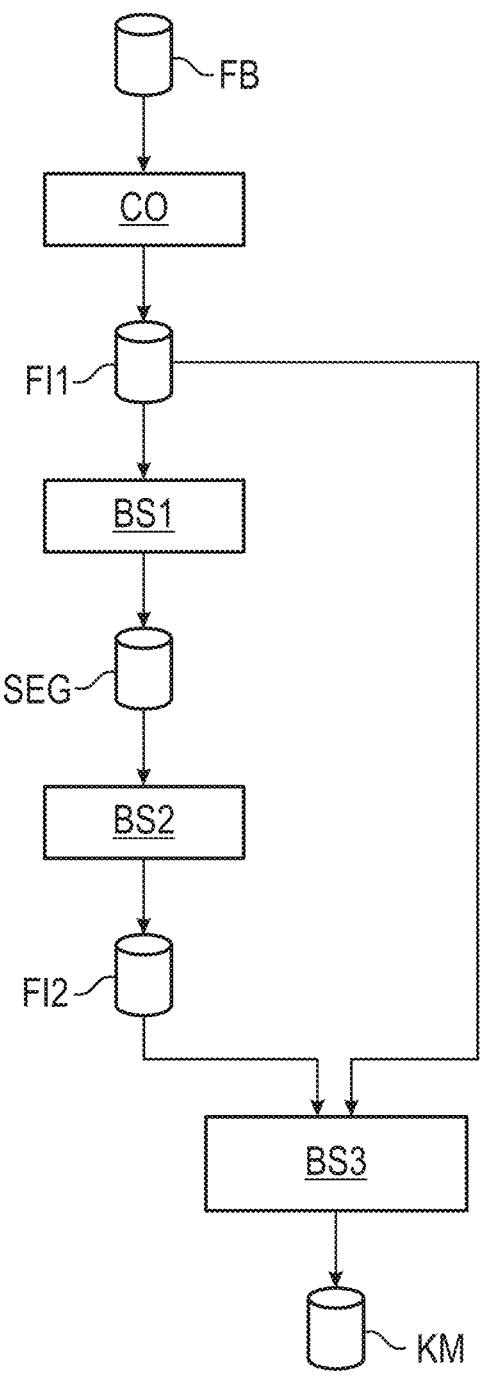
Figure 5:
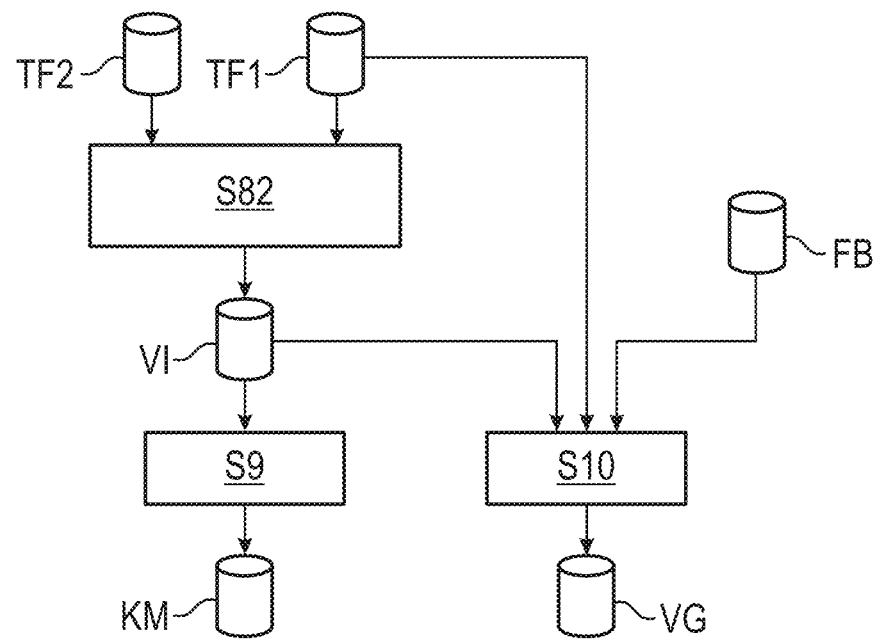
Figure 6:
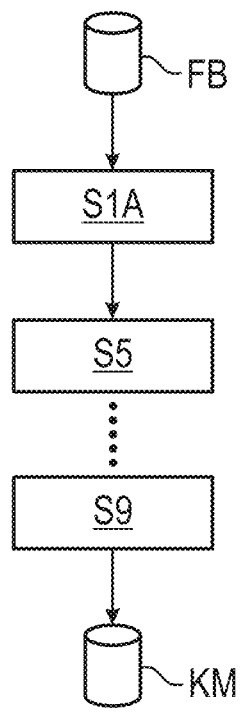
Figure 7:
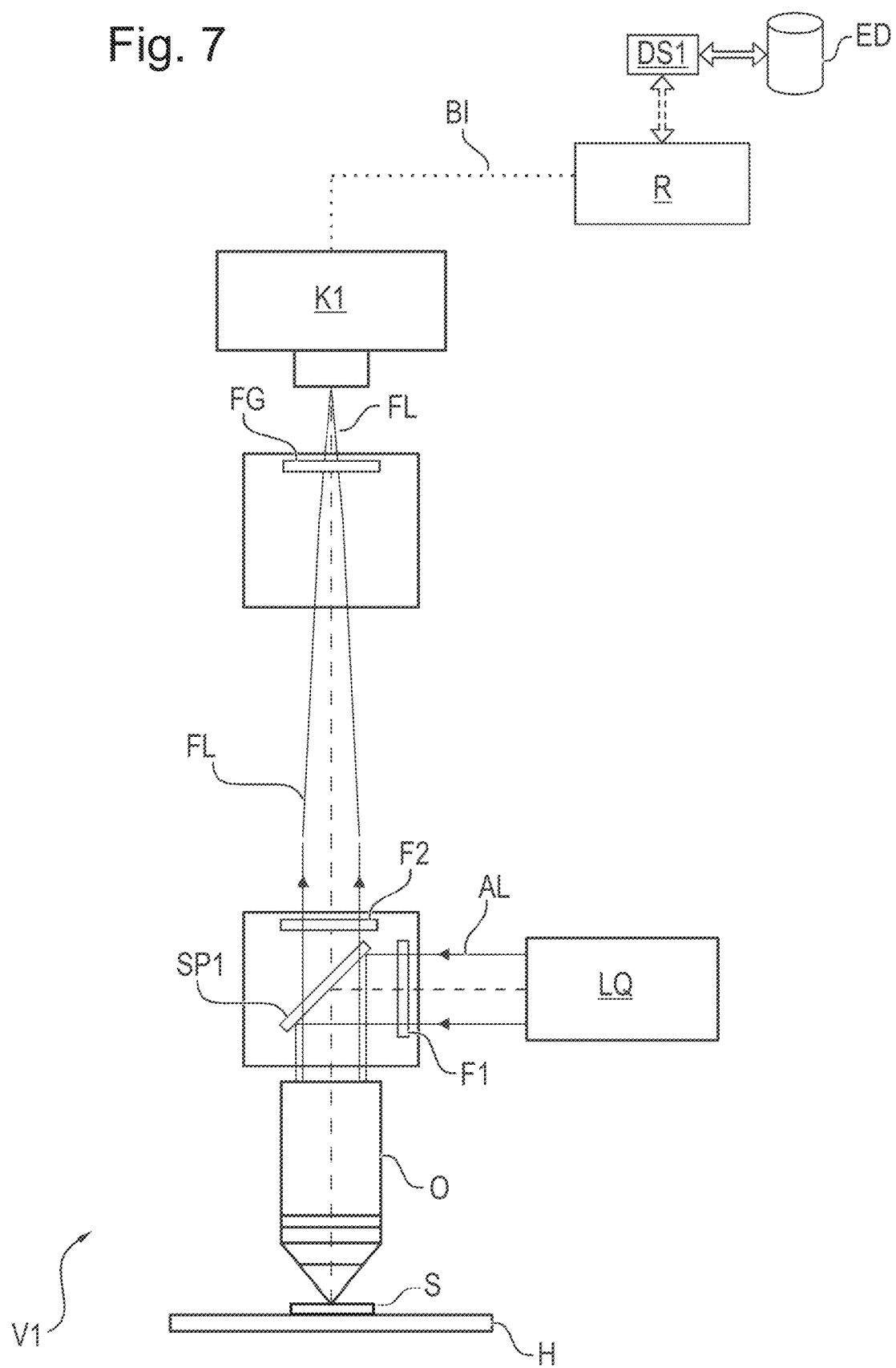
Figure 8:
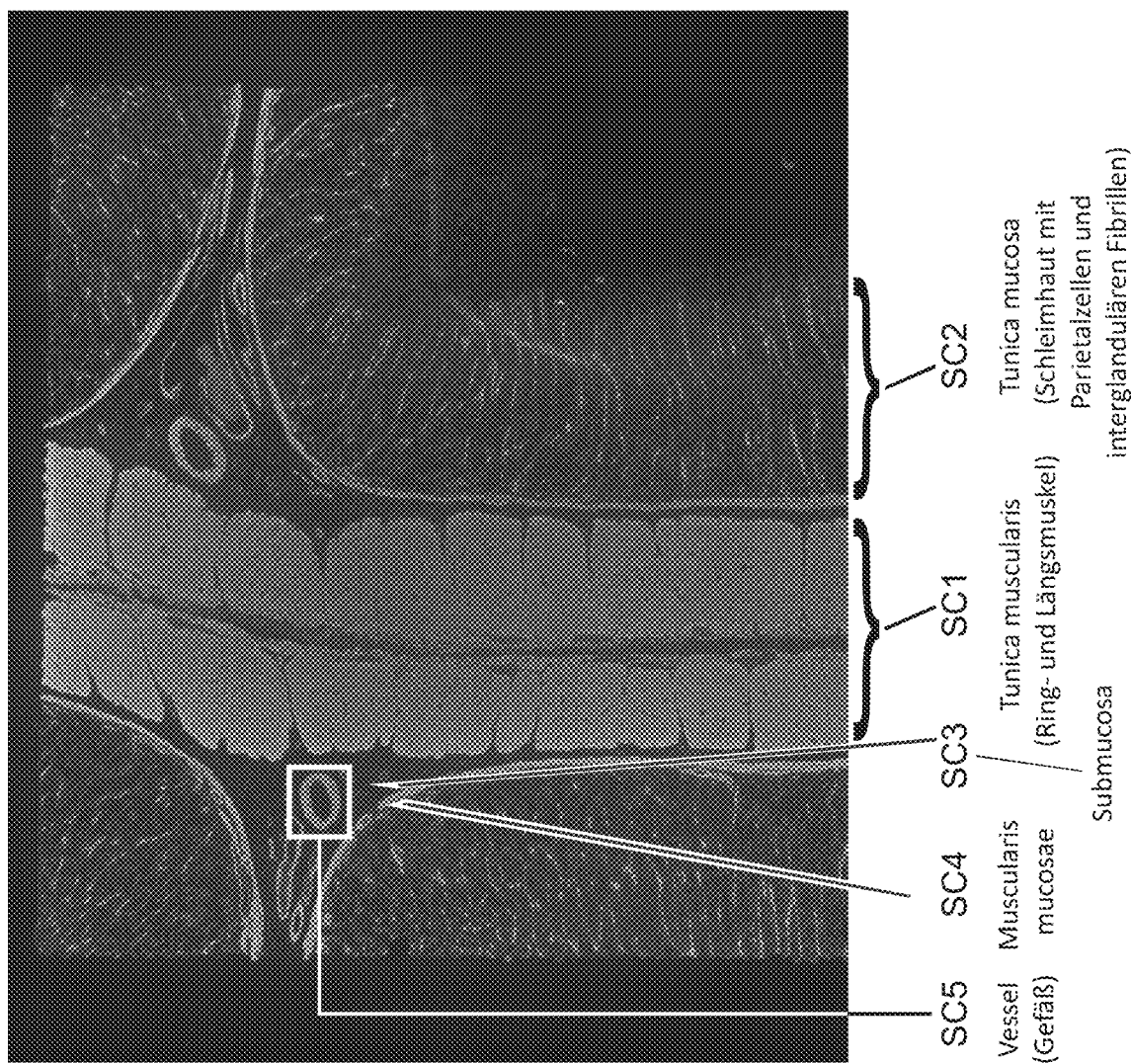
Figure 9:
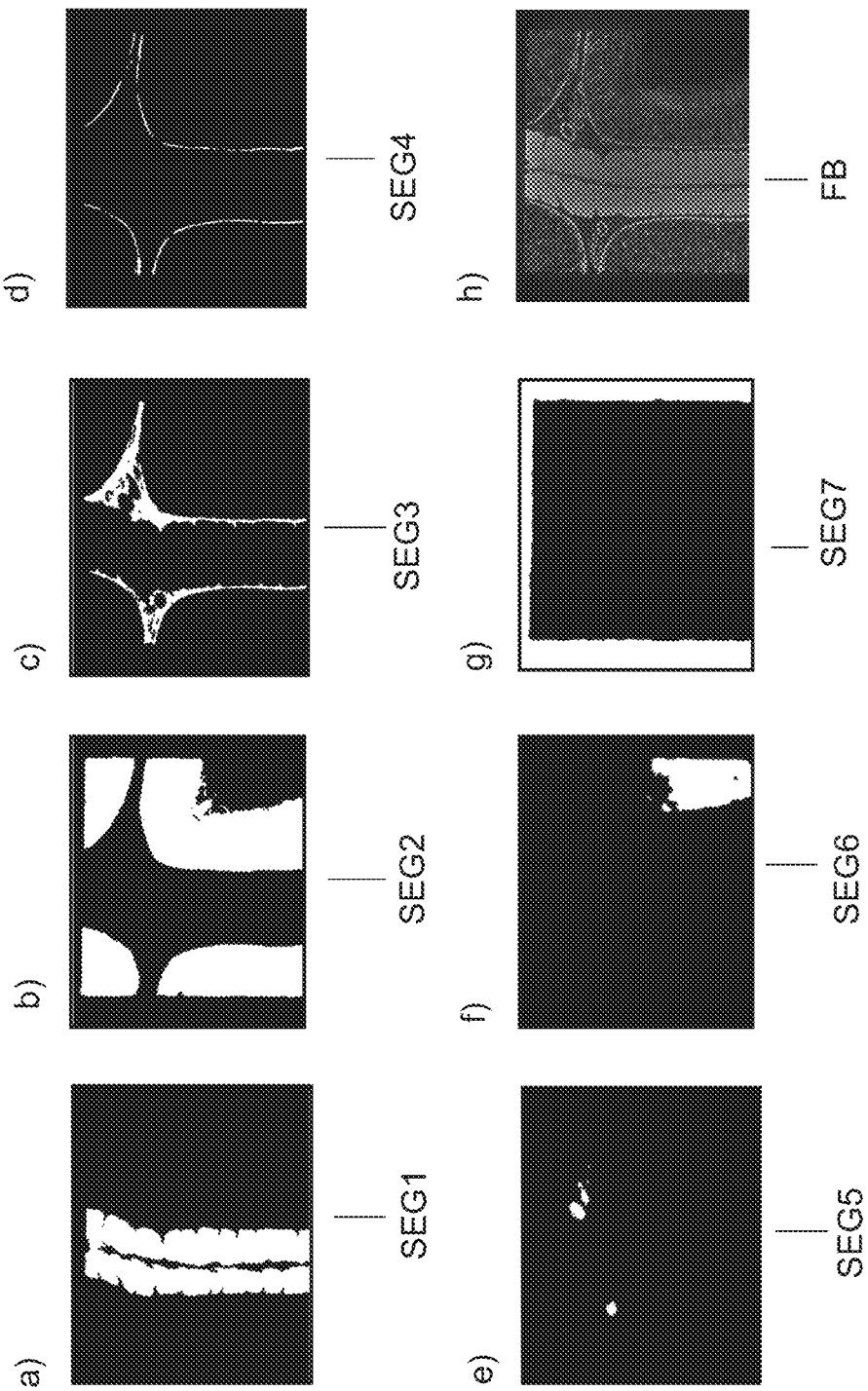
Figure 10:
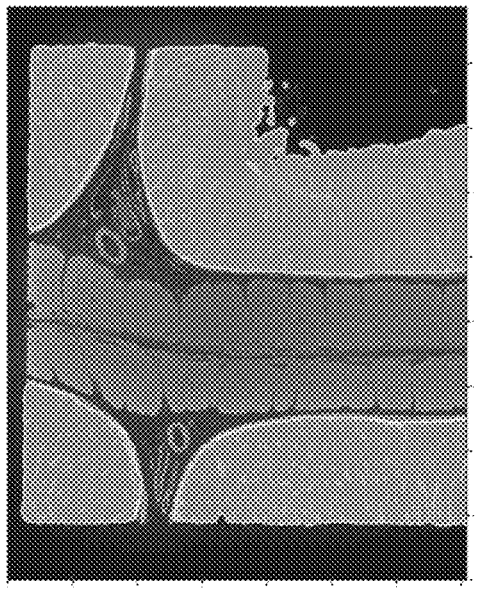
Figure 10:
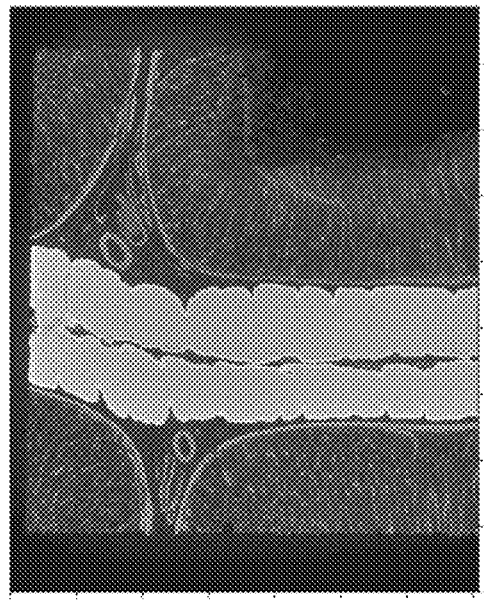
Figure 12:
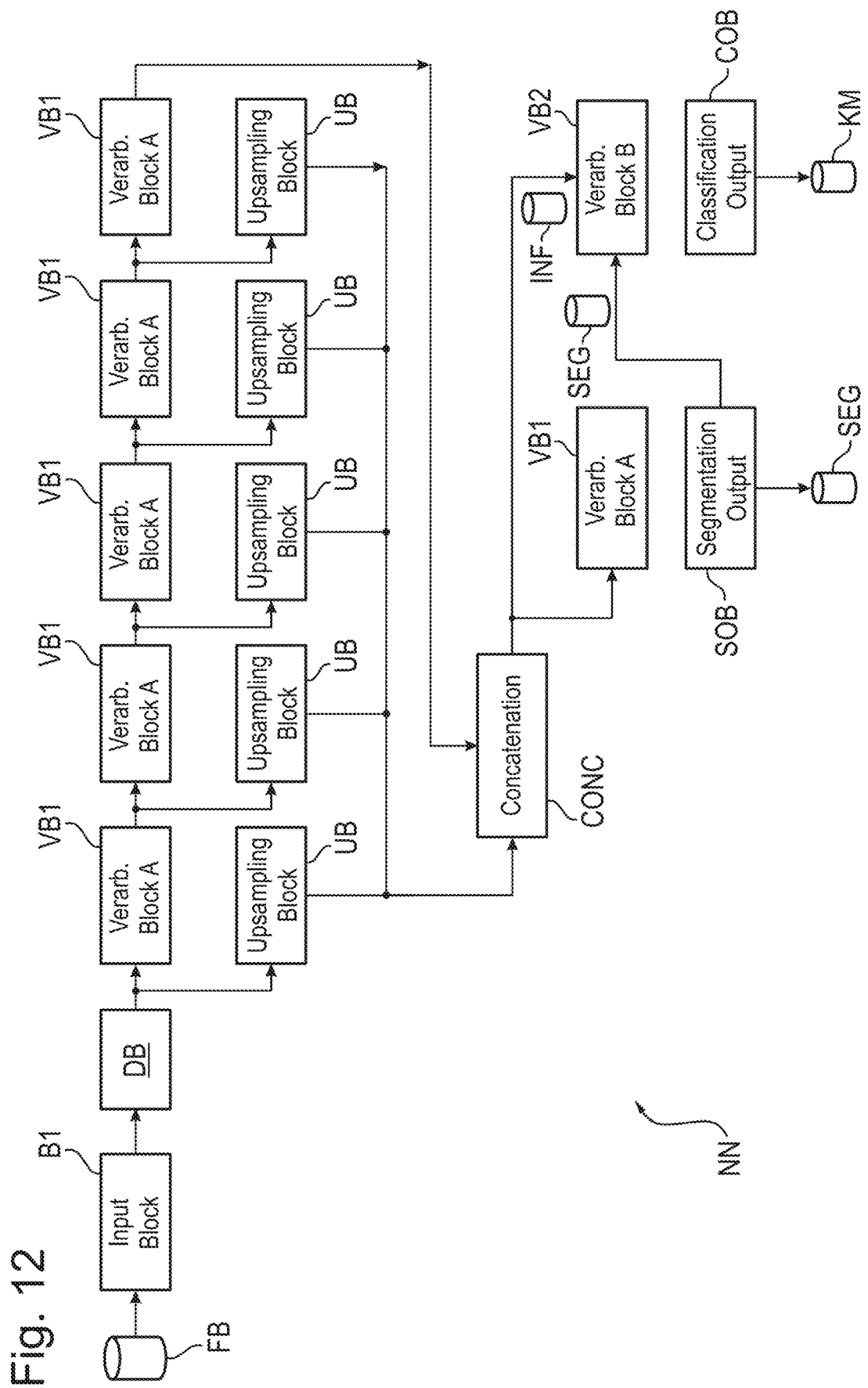
Figure 13:
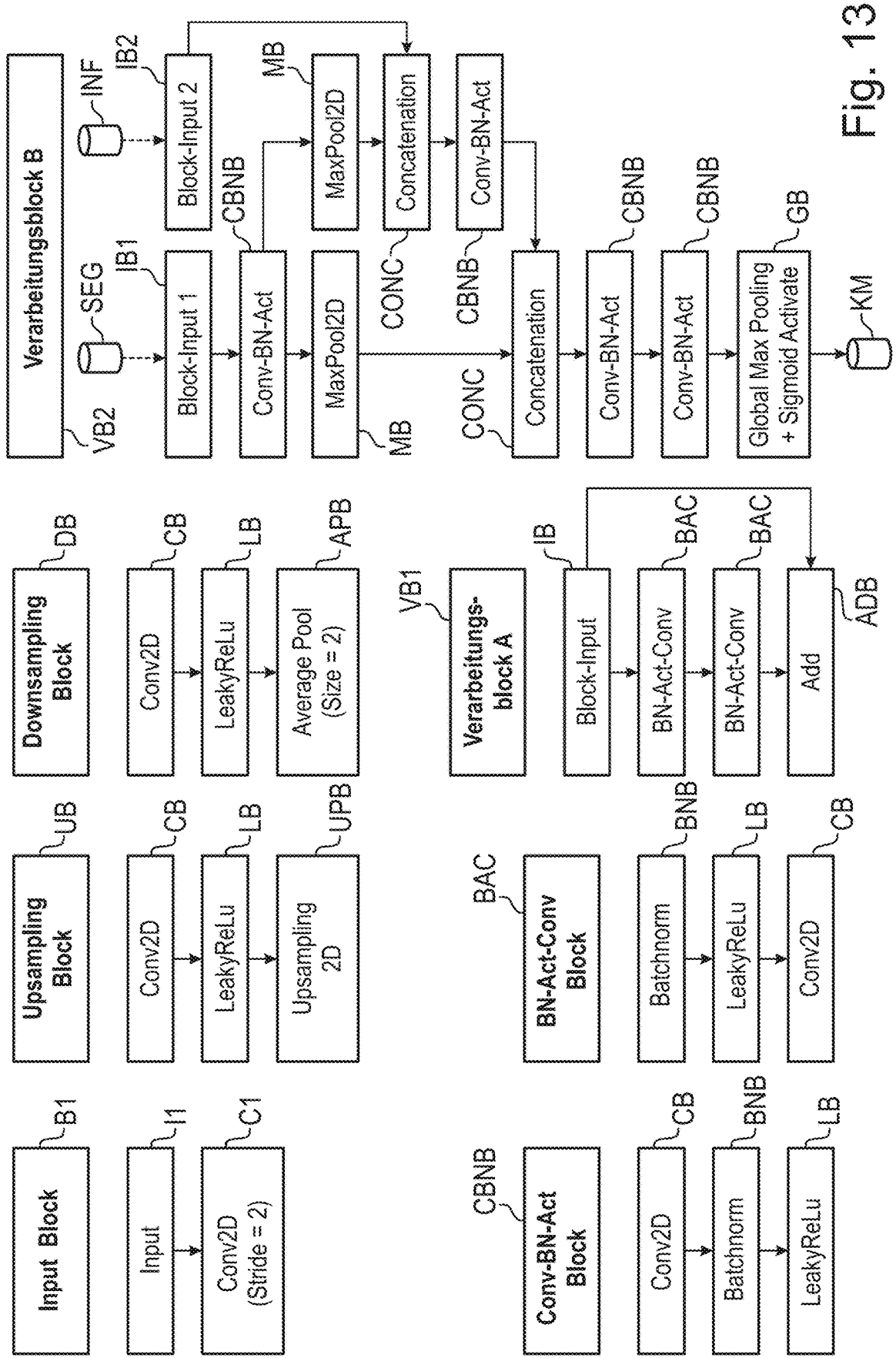

FIG. 3 shows a check of respective sub-areas with respect to respective threshold values, FIG. 4 shows one embodiment of the method according to the invention with determination steps for generation of different sets of feature information, FIG. 5 shows preferred steps for estimation of a maximum degree of dilution of a patient sample at which incubation of the organ segment with the patient sample still leads to a presence of the fluorescence pattern type, FIG. 6 shows preferred steps of a proposed method for digital image processing, FIG. 7 shows one embodiment of a proposed device, FIG. 8 shows an example organ segment having different organ layers, FIG. 9 shows a fluorescence image as from FIG. 8 together with segmentation information, FIG. 10 shows different highlighted organ layers, FIG. 11 shows experimental results, FIG. 12 shows an overview structure of one embodiment of a neural network, and FIG. 13 shows a detailed illustration of individual processing blocks of the neural network.

FIG. 7 shows a device V1 which can preferably be used to carry out the method according to the invention. The device V1 can be referred to as a fluorescence microscope. The device V1 has a holder H for a substrate S or slide which has been incubated in the manner described above. Via an optical system O, excitation light AL from an excitation light source LQ is guided towards the substrate S. Resultant fluorescence radiation FL is then back-transmitted through the optical system O and passes through the dichroic mirror SP1 and an optional optical filter F2. Preferably, the fluorescence radiation FL passes through an optical filter FG which filters out a green channel. A camera K1 is preferably a monochrome camera which then captures the fluorescence radiation FL in a green channel when an optical filter FG is present. In an alternative embodiment, the camera K1 is a colour camera which manages without use of the optical filter FG and which acquires the fluorescence image in the relevant colour channel in the form of a green channel by means of a Bayer matrix. The camera K1 provides the image information BI or the fluorescence image to a computing unit R which processes said image information BI. Preferably, the computing unit R can output or provide data ED such as, for example, a fluorescence image, measures of confidence and/or validity information via a data interface DS1.

Figure 1:
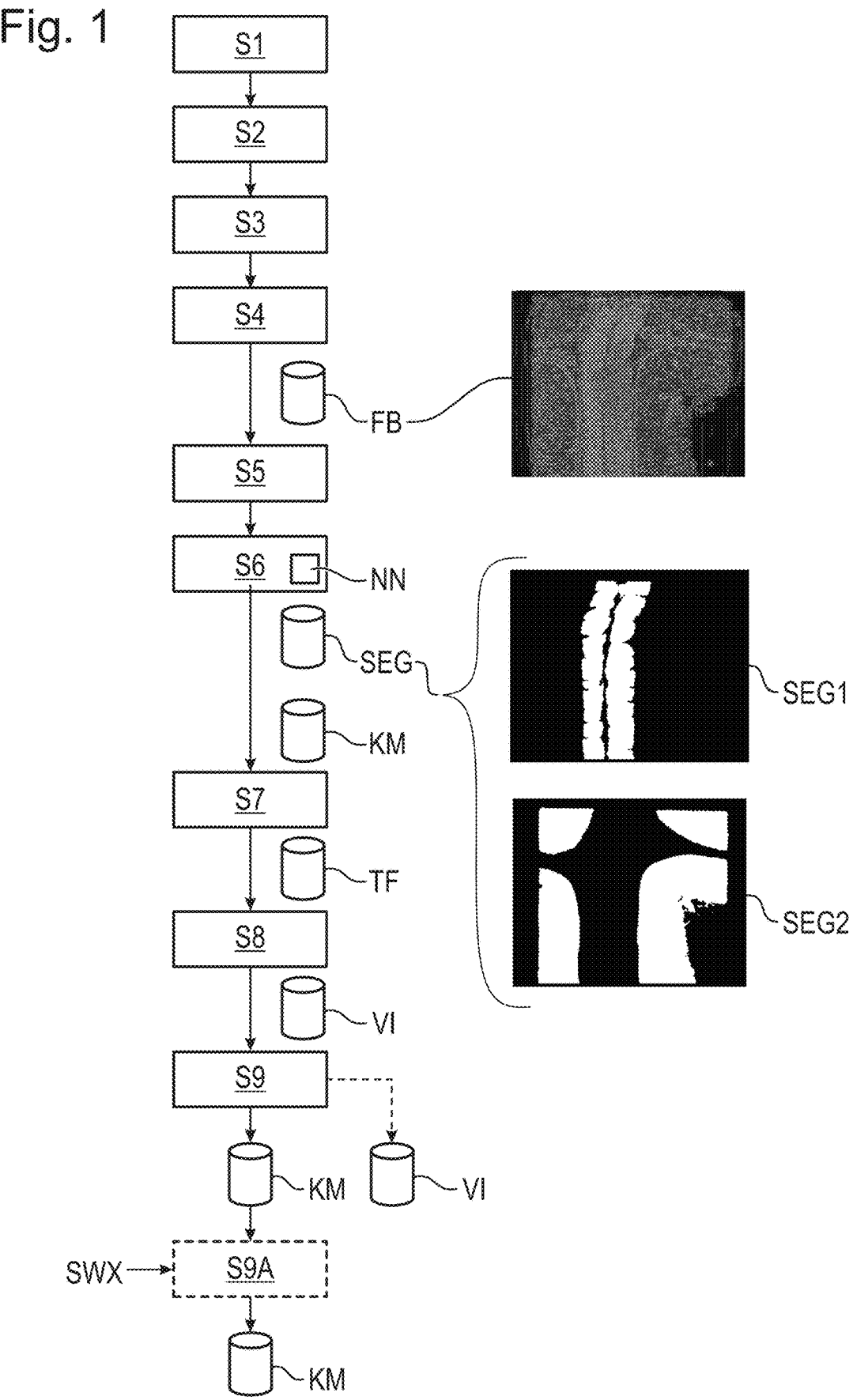
FIG. 1 shows one embodiment of the method according to the invention.

FIG. 1 shows the steps of one embodiment of the proposed method. In a step S1, the organ segment is provided on a slide. In a step S2, what takes place is incubation of the organ segment with a liquid patient sample which potentially comprises primary antibodies. In a step S3, what takes place is incubation of the organ segment with secondary antibodies which have been labelled with a fluorescent dye.

In a step S4, what takes place is acquisition of a fluorescence image of the organ segment in a colour channel corresponding to the fluorescent dye.

The result is then the fluorescence image FB, which is also depicted here for example as a data element FB. Such a fluorescence image is also depicted by way of example in FIG. 8 and in FIG. 9h.

For the fluorescence image FB, FIG. 8 illustrates the organ layer tunica muscularis as layer SC1, additionally the organ layer tunica mucosa as layer SC2, additionally the layer submucosa as layer SC3, additionally the layer muscularis mucosae as layer SC4 and additionally the vessel layer as layer SC5.

In FIG. 1, what takes place in a step S5 is the provision of the fluorescence image to a neural network.

The neural network can, for example, be used as a network NN in a step S6. In step S6, what takes place simultaneously is determination of segmentation information SEG through segmentation of the fluorescence image FB. Said segmentation information SEG is depicted here by way of example as a data element SEG and can, for example, comprise two items of sub-segmentation information SEG1 and SEG2, which are also depicted in FIGS. 9a and 9b. Furthermore, the neural network simultaneously determines a measure of confidence KM with regard to an actual presence of a fluorescence pattern type to be detected.

Preferably, the neural network NN does not just determine an individual measure of confidence KM with regard to an individual fluorescence pattern type or an individual presence of an individual fluorescence pattern type; instead, the neural network NN determines multiple measures of confidence with regard to multiple fluorescence pattern types. In such a case, the data element KM from FIG. 1 contains respective measures of confidence for respective presences of respective fluorescence pattern types. Here, the data element KM from FIG. 1 thus for example does not just comprise an individual measure of confidence, but instead, for example, thirteen measures of confidence based on thirteen different fluorescence pattern types.

Such a preferable embodiment with determination of respective measures of confidence of respective actual presences of respective fluorescence pattern types is especially advantageous because, when the neural network NN is analysing the fluorescence image FB, an occurrence of different fluorescence pattern types is then considered possible during solving and a more precise delimitation or determination of the particular fluorescence pattern type, the presence of which is to be determined, is taken into account and made possible during the analysis by the neural network. Thus, the focus here is not on a purely positive or negative decision with regard to the presence of the particular fluorescence pattern type, the detection of the presence of which is desired; instead, other possible patterns are also taken into account in the solution space.

Preferably, the neural network thus determines respective measures of confidence with respect to respective presences of respective fluorescence pattern types, with a particular measure of confidence from said measures of confidence indicating the actual presence of the particular fluorescence pattern type. Preferably, the one particular measure of confidence of the actual presence of the particular fluorescence pattern type is then output later in the course of the method depending on the validity information.

Concerning FIG. 1, it can be further stated that, in a step S7, a sub-area of the fluorescence image that is relevant to formation of the fluorescence pattern type is determined on the basis of the segmentation information SEG. In a preferred embodiment, the segmentation information SEG comprises, for example, seven different items of sub-segmentation information SEG1 to SEG7, as depicted in FIGS. 9a to 9g. Preferably, a plurality of segmentation information with regard to further layers can be taken into account. For example, segmentation information with regard to a presence of an organ layer of the stomach cavity, further segmentation information with regard to so-called artefacts and again further segmentation information with regard to other organ structures can be provided. For example, up to eleven different items of segmentation information can be provided.

FIG. 10a shows, in an overlay and in highlighted form, patterns of the organ layer tunica muscularis based on the previously determined segmentation information SEG1 from FIG. 9a. FIG. 10b shows, in an overlay, pattern formation in a region of the organ layer tunica mucosa, use being made of the segmentation information SEG2 from FIG. 9b.

For a presence of a pattern, what are especially taken into account or used are only those image regions or sub-areas relevant to the formation of the particular fluorescence pattern type. It can be at least one sub-area of the fluorescence image that corresponds to a particular corresponding organ layer. In the example of the ASMA pattern, what are used or taken into account are, for example, multiple sub-areas of the fluorescence image or multiple organ layers, for example two organ layers, namely tunica muscularis and tunica mucosa. These two layers are relevant to the formation of the fluorescence pattern type ASMA. This determination of the sub-areas of the fluorescence image or the sub-areas of the corresponding organ layers is done on the basis of the corresponding segmentation information, thus for example in segmentation information SEG1 from FIG. 9a and SEG2 from FIG. 9b. The sub-area TF1 is, for example, given by the white pixels of the segmentation information SEG1 from FIG. 9a. The sub-area TF2 is, for example, given by the white pixels of the segmentation information SEG2 from FIG. 9b.

What then takes place in a step S8 is the determination of the validity information on the basis of the previously determined at least one sub-area. FIG. 1 depicts the one or more sub-areas as a data element TF. What thus takes place is the determination of the validity information as information VI, which is depicted here as a data element VI, on the basis of the predetermined sub-area TF.

In particular, what thus takes place is determination of the respective area fractions of the respective sub-areas or the respective organ layers based on the area of the fluorescence image and the determination of the validity information on the basis of the area fractions.

This validity information VI can, for example, be a Boolean variable which assumes the value 1 if the previously determined measure of confidence KM is considered valid.

In a step S9, what then takes place, depending on the validity information VI, is output of that measure of confidence KM that is relevant to the actual presence of the particular fluorescence pattern type.

Preferably, if the validity information VI indicates an invalidity of the measure of confidence KM, the measure of confidence KM cannot be output. In particular, what can then be output instead of the measure of confidence KM is an error message, which is not explicitly depicted.

Preferably, in step S9, the validity information VI is also output.

The previously determined measure of confidence KM can, for example, be a vector of multiple scalar values, the respective vector entries representing or indicating respective measures of confidence based on respective fluorescence pattern types. Preferably, in step S9, what can be output as measure of confidence KM is only that scalar value which indicates a measure of confidence based on the fluorescence pattern to be detected, for example the ASMA pattern.

Figure 2:
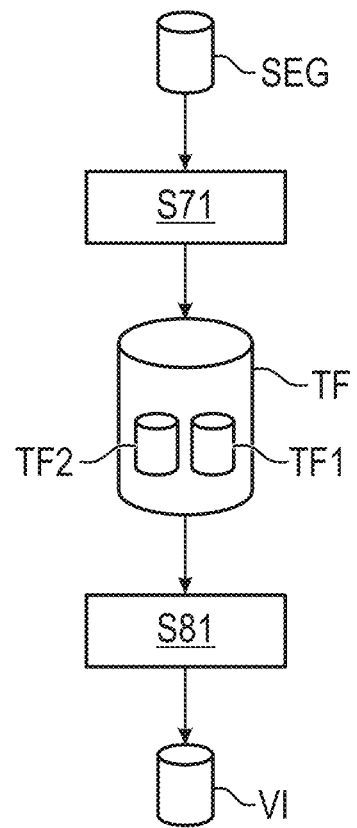
FIG. 2 shows preferred steps for determination of respective area fractions.

FIG. 2 shows a step S71, which is an alternative to step S7 and in which multiple sub-areas TF1, TF2 relevant to formation of the fluorescence pattern type are determined on the basis of the segmentation information SEG. Precisely in the example of the ASMA pattern, what arises is a previously described formation of the pattern over two different organ layers, tunica mucosae and tunica muscularis. The two organ layers must be present in the fluorescence image FB to a sufficient degree or at a sufficient area fraction.

Furthermore, FIG. 2 shows a step S81, which is an alternative to step S8 and in which the validity information VI is then determined on the basis of the multiple sub-areas TF1, TF2.

FIG. 3 shows checking of the sub-areas TF1, TF2 on the basis of respective threshold values SW1, SW2.

Step S82, which is depicted here, is a step which can be carried out as an alternative to step S81 from FIG. 2 or step S8 from FIG. 1. The validity information VI is then thus determined on the basis of the multiple sub-areas TF1, TF2 and the respective threshold values SW1, SW2. The sub-areas TF1 and TF2 have respective area fractions based on the area of the fluorescence image.

The validity information VI is then, for example, yielded by the rule $$VI = \begin{cases} 1 & \text{for } (TF1 > SW1) \land (TF2 > SW2) \\ 0 & \text{otherwise} \end{cases}$$

In short, it can be stated that, using step S82 from FIG. 3, what is thus output is the measure of confidence of the actual presence of the particular fluorescence pattern type if the respective area fractions of the respective areas TF1, TF2 exceed a respective threshold value SW1, SW2. This ensures in particular that it is not just one of the relevant sub-areas or one of the relevant organ layers that is present in the fluorescence image to a sufficient degree, but that this is the case for all relevant sub-areas or all relevant organ layers.

FIG. 4 shows preferred steps for determining different sets of feature information. FIG. 4 depicts steps which can preferably be carried out in the neural network NN.

In step CO, what takes place is processing of the fluorescence image FB by means of one or more convolutional operations. What then thus takes place in step CO is generation, on the basis of the fluorescence image FB, of a first set FI1 of a plurality of feature information in a feature space by means of the one or more convolutional operations. Thereafter, the segmentation information SEG and the measure of confidence KM are determined later on the basis of this set FI1 of feature information.

In contrast to prior art methods in which a fluorescence image FB is first analysed in a first network in order to determine segmentation information SEG in order to then place the segmentation information SEG as a so-called image mask over the fluorescence image FB and to then subsequently analyse a masked fluorescence image in a further network in order to determine the measure of confidence KM, an explicit deviation is made therefrom. The one neural network NN simultaneously determines the segmentation information SEG and the measure of confidence KM. As a result, both segmentation information SEG and measure of confidence KM can thus be simultaneously determined in a feature space and they can be mutually dependent during a training phase of the neural network NN. As a result, the segmentation information SEG thus still has an effect on the determination of the measure of confidence KM in the feature space.

After the first set of feature information FI1 has been generated, what then takes place in a determination step BS1 is the determination of the segmentation information SEG on the basis of the first set of feature information FI1. Only then is the measure of confidence KM subsequently determined on the basis of the first set of feature information FI1 and on the basis of the segmentation information SEG. Here too, the neural network NN thus simultaneously determines the segmentation information SEG and the measure of confidence KM.

Preferably, the segmentation information SEG which was determined in the determination step BS1 on the basis of the feature information FI1 is, in a determination step BS2, transformed again in the feature space into a second set of feature information FI2. What thus takes place is generation, on the basis of the segmentation information SEG, of a second set of a plurality of feature information FI2 in a feature space by means of at least one convolutional operation. Only then is the measure of confidence KM determined in the feature space in a determination step BS3 on the basis of the first set of feature information FI1 and the second set of feature information FI2.

In other words: the segmentation information SEG is thus transformed in a determination step BS2 into a feature space or feature information FI2, which is then used in the feature space together with the first feature information FI1 in order to determine the measure of confidence KM. The segmentation information SEG is thus not, as known from the prior art, directly applied to the fluorescence image FB, but transformed in the feature space as feature information FI2, and there in the feature space the segmentation information SEG is then taken into account in the determination of the measure of confidence KM, especially together with the first set of feature information FI1.

The entire fluorescence image FB is thus first transformed into the feature space as feature information FI1, and there is no back-transformation into the image space before the determination of the segmentation information SEG.

FIG. 5 shows preferred steps for estimating a maximum degree of dilution of the patient sample at which incubation of the organ segment with the patient sample still leads to a presence of the fluorescence pattern type.

The sub-areas TF1 and TF2 are used in a step S82, as previously described with regard to FIG. 3, in order to determine the validity information VI. In step S9, as previously mentioned with regard to FIG. 1, the measure of confidence KM can then be output depending on the validity information VI.

A further preferred step S10 is depicted in FIG. 5. If the validity information VI indicates that the fluorescence pattern type is determined as actually present, a degree of brightness of a sub-area in the fluorescence image can then be determined in step S10, the sub-area being potentially relevant to formation of the fluorescence pattern type. For example, it is possible here, in the case of two organ layers being relevant per se, to use just one individual organ layer. Here, the organ layer can, for example, be the tunica muscularis, for which FIG. 9a depicts a sub-area TF1.

In step S10, the maximum degree of dilution is then estimated as information VG on the basis of the sub-area TF1 and the fluorescence image FB. It is possible here, for example, in a preferred embodiment to place the segmentation information of the sub-area TF1—see FIG. 9a as segmentation information SEG1—as a mask over the fluorescence image FB and to then determine the degree of brightness or degree of intensity in this sub-area region and estimate the corresponding maximum degree of dilution on the basis of said degree of brightness.

For this purpose, pixel statistics are preferably carried out on this relevant fluorescence image region of the organ layer. What is determined is the 95% quantile of the brightness values from the sub-image TF1 of the fluorescence image. The brightness values can, for example, be quantized within the range from 0 to 255. This entire quantization range of brightness values from 0 to 255 can then be subdivided equidistantly into five sub-value ranges. The first range then ranges from 0 to 51. The other ranges follow in corresponding equidistant steps, the uppermost fifth range ending at 255. On the basis of the degree of brightness in the form of the 95% quantile, it is then possible to estimate a maximum degree of dilution of the patient sample at which incubation of the organ segment with the patient sample still leads to a presence of a fluorescence pattern type or the fluorescence pattern type. The information HI to be determined, as the 95% quantile, is then appropriately assigned to one of the sub-value ranges. The determined sub-value range or the index of the determined sub-value range determines an increment, proceeding from the present dilution of the patient sample for the generation of the fluorescence image, for defining a degree of dilution at which the patient sample would only just lead to a positive pattern or to a presence of the fluorescence pattern type. The degree of dilution VD of the sample from the incubation is thus provided as secondary information. In the case of a dilution or a degree of dilution VD of 1:10, it is then possible in the case of a series of 10-fold dilutions of the graduation 10, 32, 100, 320, 1000, 3200, 10,000, 32,000 to go further proceeding from the value of 10 on the basis of a determined increment, for example 2, and go two steps further, and to then determine a dilution of 100 as a degree of dilution at which incubation of the organ segment with the patient sample would only just lead to a presence of the fluorescence pattern type. This is then the determined degree of dilution VG.

FIG. 6 shows preferred steps of a preferred embodiment of a proposed method for digital image processing. In a step S1A, the fluorescence image FB is received. Step S1A is followed by steps S5 to S9 from FIG. 1.

There is further proposed a computer program product comprising commands which, upon execution of the program by a computer, prompt said computer to carry out the method for digital image processing of the proposed form.

According to FIG. 1, the measure of confidence KM can be checked again in a further step S9A. If the measure of confidence KM has a value which exceeds a provided threshold value SWX, the measure of confidence KM is then output. In this case, the measure of confidence KM must thus have minimum safety with regard to the presence of the particular fluorescence pattern type.

FIG. 12 shows an overview structure of a preferred embodiment of the neural network NN which receives the fluorescence image FB. In a processing block B1, the fluorescence image FB is received and pre-processed. Next is a block DB in which downsampling is carried out.

The output of the block DB is then supplied to a processing block VB1 and also to an upsampling block UB. Next are four further block arrangements in each of which the output of one processing block VB1 is supplied to a following further processing block VB1 and to an upsampling block UB.

The output of the upsampling blocks UB and the output of the last processing block VB1 are concatenated in a concatenation block CONC.

The output of the concatenation block CONC is then supplied to a processing block VB1 and to a processing block VB2.

The output of the processing block VB1 is then supplied to a block SOB for output of a segmentation event SEG. In the block SOB, the segmentation event or the segmentation information SEG is then output.

Said segmentation information SEG is also supplied to a further processing block VB2. The processing block VB2 then determines, from the output INF of the concatenation block CONC and the segmentation information SEG, the measure of confidence KM, which is output in a block COB.

FIG. 13 contains details about the described blocks from FIG. 12.

The input block B1 comprises a block I1 in which an input is received and a following block C1 in which a two-dimensional convolution is carried out. This is preferably done with stride=2.

An upsampling block UB first comprises a block CB in which a two-dimensional convolution is carried out. Next is a block LB having a LeakyReLU function. Further next is a so-called upsampling block UPB.

A downsampling block DB first comprises a block CB, which is followed by a block LB, which is then followed by a block APB in which average pooling is carried out with size=2.

A processing block VB1 first comprises a block IB in which an input is received and is then supplied to different blocks BAC, ADB. In a block BAC, what takes place is an operation sequence consisting of batchnorm, activation and convolution. In a block ADB, what takes place is element-wise addition of the multiple inputs which the block ADB has been provided with; here, the inputs are from block IB and a block BAC.

A convolution-batchnorm-activation block CBNB first comprises a block CB, then a batchnorm block BNB and then a block LB.

A batchnorm-activation-convolution block BAC first comprises a block BNB, then a block LB and then a block CB.

A processing block VB2 comprises an input block IB1 into which the segmentation information SEG enters.

A further, parallel input block IB2 receives the information INF, which is also depicted in FIG. 12. The information INF is the information which the concatenation block CONC generates and transfers to the processing block VB2.

The segmentation information SEG is then transferred into a block CBNB after the block IB1. The information generated there is transferred to a max pooling 2D block MB on the left-hand side and to a max pooling 2D block MB on the right-hand side.

In the processing strand on the left-hand side, the quantity determined by the block MB is then transferred to a concatenation block CONC. In the strand on the right-hand side, a sequence consisting of a block MB, a block CONC and a block CBNB is carried out before the correspondingly determined information is also transferred to the concatenation block CONC. Next are two CBNB blocks.

Lastly, global max pooling and sigmoid activation are carried out in a block GB. The measure-of-confidence information KM is determined as a result.

To implement one or more exemplary embodiments of the presently proposed convolutional neural network NN, a person skilled in the art can rely on a so-called open-source deep-learning library called "Keras". Detailed information can be found by a person skilled in the art under https://keras.io.

Results

The performance data were determined using 78 patient samples. Each sample was respectively titrated in 3 titration steps, followed by respective incubation of a substrate or organ segment for each titration step. Here, the incubated substrates were captured in the form of fluorescence images using the microscope EUROPattern Microscope 1.5. Each sample thus respectively yielded 3 results from the respective 3 titration stages. If, as a result of the proposed method, a presence of the fluorescence pattern type was positively detected for at least one of the 3 fluorescence images of the particular sample, the conclusion drawn was an in-principle presence of the fluorescence pattern type.

In relation this, the table TAB from FIG. 11 shows that, out of 21 samples which are actually positive, the proposed method identified 19 samples as positive and 2 samples were incorrectly identified as negative. The table from FIG. 11 further shows that, out of 57 samples which are actually negative, the proposed method identified 55 samples as negative and 2 samples were incorrectly identified as positive. This yields an analytical sensitivity of 0.90. This also yields an analytical specificity of 0.96.

Although some aspects have been described in connection with a device, it is self-evident that said aspects are also a description of the corresponding methods, and so a block or a component of a device can also be understood as a corresponding method step or as a feature of a method step. By analogy, aspects which have been described in connection with a method step or as a method step are also a description of a corresponding block or detail or feature of a corresponding device.

Depending on the particular implementation requirements, it is possible for exemplary embodiments of the invention to realize the computing unit R or the data network device in hardware and/or in software. Here, a presently mentioned computing unit R can be realized as at least one computing unit or else by an association of multiple computing units. Implementation can be achieved using a digital storage medium, for example a floppy disk, a DVD, a Blu-Ray Disc, a CD, a ROM, a PROM, an EPROM, an EEPROM or a FLASH memory, a hard disk or some other magnetic or optical memory, which stores electronically readable control signals which cooperate or can cooperate with a programmable hardware component such that the method in question is carried out.

A programmable hardware component can be formed as a computing unit by a processor, a central processing unit (CPU), a computer, a computer system, an application-specific integrated circuit (ASIC), an integrated circuit (IC), a system on a chip (SOC), a programmable logic element or a field-programmable gate array with a microprocessor (FPGA).

The digital storage medium can therefore be machine-readable or computer-readable. Some exemplary embodiments thus comprise a data carrier having electronically readable control signals capable of cooperating with a programmable computer system or a programmable hardware component such that one of the methods described herein is carried out.

In general, exemplary embodiments or parts of exemplary embodiments of the present invention can be implemented as a program, firmware, computer program or computer program product containing a program code or as data, the program code or the data being effective in carrying out one of the methods or part of a method when the program runs on a processor or a programmable hardware component.

The invention claimed is:

1. Method for detecting at least one potential presence of at least one fluorescence pattern type on an organ segment via immunofluorescence microscopy and via digital image processing, comprising providing the organ segment comprising multiple organ layers on a slide, incubating the organ segment with a liquid patient sample which potentially comprises primary antibodies, incubating the organ segment with secondary antibodies which have been labelled with a fluorescent dye, acquiring a fluorescence image (FB) of the organ segment in a colour channel corresponding to the fluorescent dye, providing the fluorescence image (FB) to a neural network (NN), simultaneously determining, by means of the one neural network (NN), segmentation information (SEG) through segmentation of the fluorescence image (FB) and, furthermore, a measure of confidence (KM) indicating an actual presence of the fluorescence pattern type, determining, on the basis of the segmentation information (SEG), multiple sub-areas (TF1, TF2) of the fluorescence image (FB) that are relevant to formation of the fluorescence pattern type, wherein said sub-areas are organ layers of said organ segment, determining respective area fractions of the respective sub-areas (TF1, TF2) based on the area of the fluorescence image (FB), determining, on the basis of the previously determined area fractions, validity information (VI) indicating a degree of a validity of the measure of confidence (KM), outputting the measure of confidence (KM) of the actual presence of the fluorescence pattern type depending on the validity information (VI).

2. Method according to claim 1, further comprising determining the validity information (VI) on the basis of the area fractions and on the basis of respective threshold values, outputting the measure of confidence (KM) of the actual presence of the fluorescence pattern type if the respective area fractions exceed a respective threshold value (SW1, SW2).

3. Method according to claim 1, wherein the neural network (NN)
first generates, on the basis of the fluorescence image (FB), a first set (FI1) of a plurality of feature information in a feature space by means of at least one or more convolutional operations
and then determines, on the basis of the first set (FI1) of feature information, the segmentation information (SEG) and the measure of confidence (KM).

4. Method according to claim 1, wherein the neural network (NN)
first generates, on the basis of the fluorescence image (FB), a first set (FI1) of a plurality of feature information in a feature space by means of one or more convolutional operations
furthermore determines, on the basis of the first set (FI1) of feature information, the segmentation information (SEG)
and furthermore determines, on the basis of the first set (FI1) of feature information and on the basis of the segmentation information (SEG), the measure of confidence (KM).

5. Method according to claim 1, wherein the neural network (NN)
first generates, on the basis of the fluorescence image (FB), a first set (FI1) of a plurality of feature information in a feature space by means of one or more convolutional operations,
furthermore determines, on the basis of the first set (FI1) of feature information, the segmentation information,
furthermore generates, on the basis of the segmentation information (SEG), a second set (FI2) of a plurality of feature information in a feature space by means of at least one convolutional operation
and furthermore determines, on the basis of the first set (FI1) of feature information and the second set (FI2) of feature information, the measure of confidence (KM).

6. Method according to claim 1, further comprising
determining, on the basis of the segmentation information (SEG), multiple sub-areas (TF1, TF2) of the fluorescence image (FB) that are relevant to formation of the fluorescence pattern type,
and, in the event of the fluorescence pattern type being determined as actually present, determining a degree of brightness of one of the sub-areas (TF1) in the fluorescence image (FB) that is potentially relevant to formation of the fluorescence pattern type,
and estimating a maximum degree of dilution (VG) of the patient sample at which incubation of the organ segment with the patient sample still leads to a presence of a fluorescence pattern type or the fluorescence pattern type.

7. Device (V1) for detecting at least one potential presence of at least one fluorescence pattern type on an organ segment comprising multiple organ layers via immunofluorescence microscopy and via digital image processing, comprising
a holding device (H) for a slide containing an organ segment(S) which has been incubated with a patient sample potentially comprising primary antibodies and furthermore with secondary antibodies which have each been labelled with a fluorescent dye,
at least one image acquisition unit (K1, K2) for acquiring a fluorescence image (FB) of the organ segment(S) in a colour channel corresponding to the fluorescent dye,
and further comprising at least one computing unit (R) designed
to provide the fluorescence image (FB) to a neural network (NN),
to simultaneously determine, by means of the one neural network (NN), segmentation information (SEG) through segmentation of the fluorescence image (FB) and, furthermore, a measure of confidence (KM) indicating an actual presence of the fluorescence pattern type,
to determine, on the basis of the segmentation information (SEG), multiple sub-areas (TF1, TF2) of the fluorescence image (FB) that are relevant to formation of the fluorescence pattern type, wherein said sub-areas are organ layers of said organ segment,
determining respective area fractions of the respective sub-areas (TF1, TF2) based on the area of the fluorescence image (FB)
to determine, on the basis of the previously determined area fractions (TF4, TF2), validity information (VI) indicating a degree of a validity of the measure of confidence (KM),
and to output the measure of confidence (KM) of the actual presence of the fluorescence pattern type depending on the validity information (VI).

8. Method for digital image processing, comprising
receiving a fluorescence image representing staining of an organ segment(S) comprising multiple organ layers due to a fluorescent dye,
providing the fluorescence image (FB) to a neural network (NN),
simultaneously determining, by means of the one common neural network (NN), segmentation information (SEG) through segmentation of the fluorescence image (FB) and a measure of confidence (KM) indicating an actual presence of the fluorescence pattern type,
determining, on the basis of the segmentation information (SEG), multiple sub-areas (TF1, TF2) of the fluorescence image (FB) that are relevant to formation of the fluorescence pattern type, wherein said sub-areas are organ layers of said organ segment,
determining respective area fractions of the respective sub-areas (TF1, TF2) based on the area of the fluorescence image (FB),
determining, on the basis of the previously determined multiple sub-areas (TF1, TF2), validity information (VI) indicating a degree of a validity of the measure of confidence (KM),
outputting the measure of confidence (KM) of the actual presence of the fluorescence pattern type depending on the validity information (VI).

9. Computer program product comprising commands which, upon execution of the program by a computer, prompt said computer to carry out the method for digital image processing according to claim 8.

* * * * *